(12) United States Patent
Tanaka et al.

(10) Patent No.: US 10,779,973 B2
(45) Date of Patent: Sep. 22, 2020

(54) STENT

(71) Applicant: GOODMAN CO., LTD., Nagoya-shi, Aichi-ken (JP)

(72) Inventors: Takaharu Tanaka, Seto (JP); Yumiko Nomura, Seto (JP)

(73) Assignee: GOODMAN CO., LTD., Nagoya-shi, Aichi-ken (JP)

( * ) Notice: Subject to any disclaimer, the term of this patent is extended or adjusted under 35 U.S.C. 154(b) by 102 days.

(21) Appl. No.: 15/699,296

(22) Filed: Sep. 8, 2017

(65) Prior Publication Data

US 2017/0367856 A1    Dec. 28, 2017

Related U.S. Application Data

(63) Continuation-in-part of application No. PCT/JP2016/058220, filed on Mar. 16, 2016.

(30) Foreign Application Priority Data

Mar. 18, 2015  (JP) ................... 2015-054221

(51) Int. Cl.
*A61F 2/82*   (2013.01)
*A61F 2/89*   (2013.01)
(Continued)

(52) U.S. Cl.
CPC .................. *A61F 2/89* (2013.01); *A61F 2/86* (2013.01); *A61F 2/95* (2013.01);
(Continued)

(58) Field of Classification Search
CPC ........ A61F 2/82–945; A61F 2/24–2439; A61F 2/2475; A61F 2250/0039;
(Continued)

(56) References Cited

U.S. PATENT DOCUMENTS

| 6,863,685 B2 | 3/2005 | Davila et al. |
| 7,462,190 B2 | 12/2008 | Lombardi |

(Continued)

FOREIGN PATENT DOCUMENTS

| CN | 101415380 A | 4/2009 |
| CN | 103930043 A | 7/2014 |

(Continued)

OTHER PUBLICATIONS

International Search Report of PCT/JP2016/058220 dated Jun. 14, 2016.

(Continued)

*Primary Examiner* — Yashita Sharma
*Assistant Examiner* — Rebecca S Preston
(74) *Attorney, Agent, or Firm* — Banner & Witcoff, Ltd.

(57) ABSTRACT

A stent includes a cylindrical main body portion, a linkage portion, and a marker attachment portion. The main body portion extends in an axial direction. The linkage portion extends from an end of the main body portion in the axial direction. The marker attachment portion is linked to the main body portion through the linkage portion. The linkage portion includes a bent portion tilting the marker attachment portion outward in a radial direction of the main body portion.

14 Claims, 6 Drawing Sheets

(51) Int. Cl.
*A61F 2/86* (2013.01)
*A61F 2/848* (2013.01)
*A61F 2/915* (2013.01)
*A61F 2/95* (2013.01)

(52) U.S. Cl.
CPC . *A61F 2002/826* (2013.01); *A61F 2002/8483* (2013.01); *A61F 2002/91575* (2013.01); *A61F 2210/0014* (2013.01); *A61F 2220/0008* (2013.01); *A61F 2220/0016* (2013.01); *A61F 2230/0069* (2013.01); *A61F 2250/0029* (2013.01); *A61F 2250/0036* (2013.01); *A61F 2250/0039* (2013.01)

(58) Field of Classification Search
CPC .... A61F 2250/0096–0098; A61F 2/848–8486; A61F 2220/0018
See application file for complete search history.

(56) References Cited

U.S. PATENT DOCUMENTS

| | | | |
|---|---|---|---|
| 8,870,947 B2 | 10/2014 | Shaw | |
| 9,333,101 B2 | 5/2016 | Shaw | |
| 9,730,818 B2 | 8/2017 | Giasolli et al. | |
| 2002/0143386 A1 | 10/2002 | Davila et al. | |
| 2004/0015228 A1 | 1/2004 | Lombardi et al. | |
| 2004/0254627 A1* | 12/2004 | Thompson | A61F 2/91 623/1.11 |
| 2005/0222668 A1 | 10/2005 | Schaeffer et al. | |
| 2007/0067016 A1 | 3/2007 | Jung | |
| 2007/0129786 A1 | 6/2007 | Beach et al. | |
| 2007/0239261 A1 | 10/2007 | Bose et al. | |
| 2009/0069881 A1* | 3/2009 | Chalekian | A61F 2/856 623/1.16 |
| 2010/0292778 A1* | 11/2010 | Roeder | A61F 2/91 623/1.17 |
| 2013/0073029 A1 | 3/2013 | Shaw | |
| 2013/0144375 A1 | 6/2013 | Giasolli et al. | |
| 2013/0268055 A1 | 10/2013 | Cottone | |
| 2015/0039084 A1* | 2/2015 | Levi | A61B 17/0057 623/2.38 |
| 2015/0051695 A1 | 2/2015 | Shaw | |
| 2016/0228267 A1* | 8/2016 | Pacetti | A61F 2/82 |
| 2018/0110634 A1 | 4/2018 | Giasolli et al. | |

FOREIGN PATENT DOCUMENTS

| | | |
|---|---|---|
| CN | 104159544 A | 11/2014 |
| JP | 2004-506477 A | 3/2004 |
| JP | 2004524916 A | 8/2004 |
| JP | 4722378 B2 | 7/2011 |
| JP | 2014-531247 A | 11/2014 |
| JP | 2015506760 A | 3/2015 |
| WO | 2002/15820 A2 | 2/2002 |
| WO | 2014-141239 A1 | 9/2014 |

OTHER PUBLICATIONS

Jul. 3, 2018—(CN) First Office Action—App 201680008410.8.
Sep. 19, 2017—IPRP and Written Opinion—App PCT/JP2016/058220.
May 8, 2018—(JP) Notification of Reason for Rejection—App 2015/054221.
Oct. 23, 2018—(JP) Notification of Reason for Rejection—App 2015-054221.
Nov. 19, 2018—(EP) Extended Search Report—App 16764991.2.
Mar. 22, 2019—(CN) The Second Office Action—App 201680008410.8.
Jul. 29, 2019—(CN) Rejection Decision—App 201680008410.8, Eng Tran.

* cited by examiner

STENT

CROSS-REFERENCE TO RELATED APPLICATION

This application is a continuation-in-part of International Application No. PCT/JP2016/058220, filed Mar. 16, 2016, which claims priority from Japanese Patent Application No. 2015-054221, filed on Mar. 18, 2015. The disclosure of the foregoing application is hereby incorporated by reference in its entirety.

BACKGROUND

The present disclosure relates to a stent.

A stent is known as a medical device that, in a case where a constricted portion forms in a blood vessel, the urethra, or another tubular cavity of an internal organ in a living organism, is used to dilate the constricted portion. The stent is used in various different locations in the living organism, such as in the heart, in the brain, and the like. However, if the stent is implanted in a body part that moves in a plurality of directions, such as a leg or the like, the stent tends to suffer damage in response to the movement. Therefore, in a case where a constricted portion forms in such a body part, a dilation procedure that uses a balloon instead of the stent is often performed.

SUMMARY

Incidentally, in a case where a dilation procedure that uses a balloon is performed, detachment may occur in the blood vessel wall. In that case, complications may occur, such as obstruction of the blood vessel by the detached portion of the wall, for example. Accordingly, in a case where detachment has occurred in the blood vessel wall, a short stent, whose length in the axial direction is short, may be implanted in the body, because it is thought that the detached portion may be supported by the short stent. The use of the short stent may inhibit the occurrence of the complication mentioned above, in which the blood vessel is obstructed by the detached portion. The use of the short stent may also inhibit the occurrence of damage when the stent is implanted in a body part that moves in a plurality of directions, such as a leg or the like.

However, this sort of short stent may shift position after being implanted in the body. In a case where the stent has shifted position, the detached portion may cease to be supported by the stent, and the complication mentioned above may be caused by the detached portion.

Furthermore, the problem of position shifting is not limited to the short stent and is a problem that may occur with all types of stents.

Various embodiments of the broad principles derived herein provide a stent that is capable of inhibiting shifting of position within the body.

Embodiments provide a stent that includes a cylindrical main body portion, a linkage portion, and a marker attachment portion. The main body portion extends in an axial direction. The linkage portion extends from an end of the main body portion in the axial direction. The marker attachment portion is linked to the main body portion through the linkage portion. The linkage portion includes a bent portion tilting the marker attachment portion outward in a radial direction of the main body portion.

BRIEF DESCRIPTION OF THE DRAWINGS

Embodiments will be described below in detail with reference to the accompanying drawings in which.

DETAILED DESCRIPTION

Figure 1:
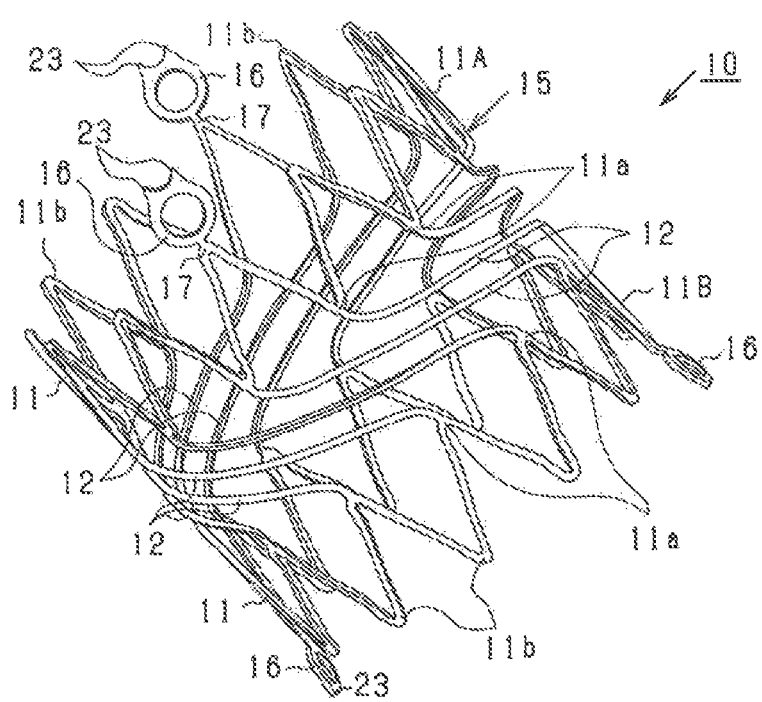
FIG. 1 is an oblique view that shows the structure of a stent.
Figure 2:
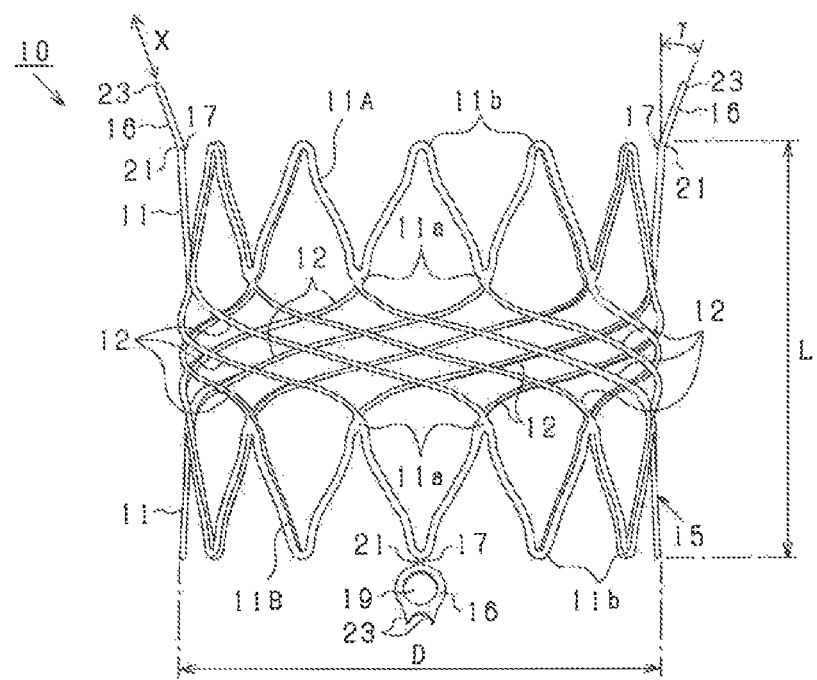
FIG. 2 is a front view that shows the structure of the stent.
Figure 3:
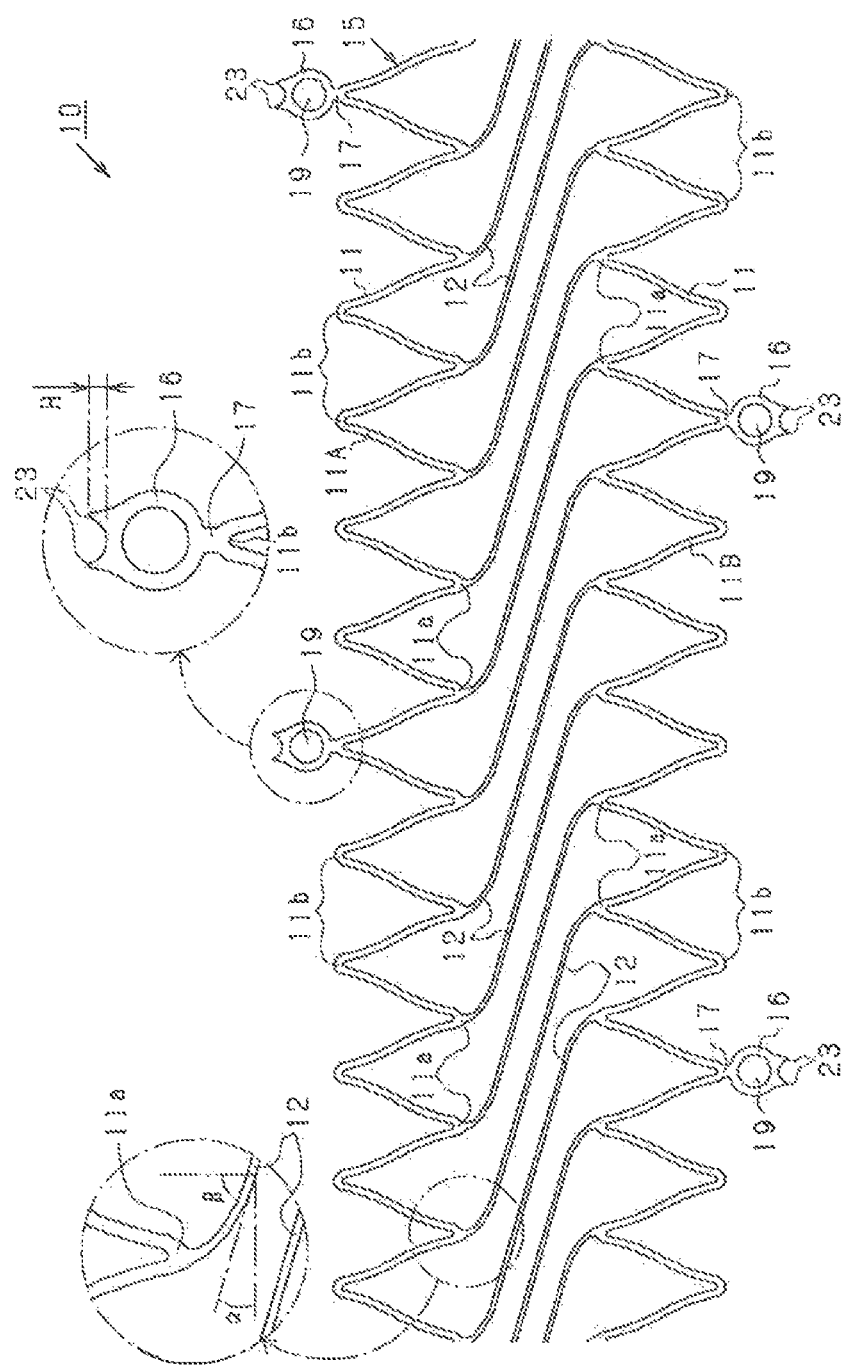
FIG. 3 is an opened-up view that shows an opened-up state of the stent.

Hereinafter, an embodiment will be explained with reference to the drawings. The present embodiment will be explained using as an example a self-expanding stent that expands based on its own elastic force. FIG. 1 is an oblique view that shows the structure of the stent. FIG. 2 is a front view that shows the structure of the stent. FIG. 3 is an opened-up view that shows an opened-up state of the stent.

As shown in FIGS. 1 to 3, a stent 10 is formed from a plurality of linear elements into an overall cylindrical shape (tubular shape). The stent 10 is formed from an elastic metal material. Specifically, the stent 10 is formed from a nickel-titanium (Ni—Ti) alloy, which is a type of ultra-elastic alloy. The stent 10 is a self-expanding stent that, by its own elastic force (energizing force), changes its shape from a contracted state to an expanded state. The expanded state is a state in which the outside diameter of the stent 10 is greater than the outside diameter of the stent 10 in the contracted state. Note that the stent 10 may also be formed from a different ultra-elastic alloy, such as a gold-cadmium alloy, a copper-aluminum-nickel alloy, a nickel-titanium-cobalt alloy or the like.

The stent 10 is provided with a main body portion 15 and a marker attachment portion 16. The main body portion 15 is provided with a plurality of ring portions 11, which are arrayed in an axial direction, and a plurality of connection portions 12, which connect the ring portions 11 that are adjacent to one another. In the present embodiment, the number of the ring portions 11 is two. The ring portions 11 are formed such that the linear elements form a circular ring around an axis line of the stent 10. Note that in the explanation that follows, for the sake of convenience, the two ring portions 11 will be distinguished by calling one of the ring portions 11 the ring portion 11A and the other one of the ring portions 11 the ring portion 11B.

The ring portions 11 are portions that form wavy lines along a circumferential direction (the direction around the axis line). At both edges in the axial direction, the ring portions 11 have shapes that alternately bend back and forth. Accordingly, in each one of the ring portions 11A, 11B, apices 11a, 11b are formed at both edges in the axial direction. More specifically, the apices 11a are formed on the edges of the ring portions 11A, 11B that are closer to one another, and the apices 11b are formed on the edges of the ring portions 11A, 11B that are farther from one another. The ring portions 11A, 11B also have identical shapes, and they are disposed such that their orientations are the reverse of one another in the axial direction. Accordingly, the apices 11a of the ring portion 11A and the apices 11a of the ring portion 11B are disposed in the same positions in the circumferential direction, and the apices 11b of the ring portion 11A and the apices 11b of the ring portion 11B are disposed in the same positions in the circumferential direction.

Each one of the plurality of the connection portions 12 is formed from a linear element. Each one of the plurality of the connection portions 12 is provided between the mutually adjacent ring portions 11A, 11B. The connection portions 12 are disposed at specified intervals in the circumferential direction of the ring portions 11A, 11B and connect the mutually adjacent ring portions 11A, 11B. In the present embodiment, the connection portions 12 are disposed at equal intervals in the circumferential direction. The plurality of the connection portions 12 connect the apices 11a of the ring portion 11A to the apices 11a of the ring portion 11B. That is, the connection portions 12 extend from all of the apices 11a of the ring portions 11A, 11B. In this manner, one end of each one of the plurality of the connection portions 12 is connected to one of the apices 11a of the ring portion 11A, and the other end of each one of the connection portions 12 is connected to one of the apices 11a of the ring portion 11B.

Note that in the present embodiment, the linear elements that form the connection portions 12 are narrower than the linear elements that form the ring portions 11. However, the linear elements of the connection portions 12 may also be of the same thickness as the linear elements of the ring portions 11, and they may also be thicker than the linear elements of the ring portions 11.

Each one of the plurality of the connection portions 12 extends in the axial direction along the circumferential direction of the ring portions 11 (the stent 10). That is, each one of the plurality of the connection portions 12 extends in a specified direction that includes a circumferential direction component and an axial direction component. Accordingly, each one of the connection portions 12 extends in a direction that is inclined in relation to the circumferential direction and the axial direction. In this case, each one of the connection portions 12 connects the apices 11a of the ring portions 11A, 11B that are disposed in different positions in the circumferential direction.

As shown in FIG. 3, each one of the connection portions 12 is disposed such that an inclination angle α in relation to the circumferential direction is less than an inclination angle β in relation to the axial direction. Note that the sum of the inclination angle α and the inclination angle β is 90 degrees. In the present embodiment, the inclination angle α is set to 20 degrees, and the inclination angle β is set to 70 degrees. Setting the inclination angles α, β in this manner ensures that the length of the connection portion 12 is sufficiently longer than the distance between the adjacent ring portions 11A, 11B.

Note that it is not absolutely necessary to set the inclination angles α, β to the values stated above, but it is preferable for the inclination angle α to be set to not greater than 30 degrees.

Setting the inclination angles α, β of the connection portion 12 as described above ensures that the distance between the opposite ends of the connection portion 12 in the circumferential direction is greater than the distance between the opposite ends of the connection portion 12 in the axial direction. Furthermore, the intervals between the connection portions 12 are less than the intervals between the apices 11b in the circumferential direction of the ring portions 11. More specifically, the intervals between the connection portions 12 are not greater than half of the intervals between the apices 11b. Note that the intervals between the connection portions 12 are the intervals in a direction that is orthogonal to a length direction of the connection portions 12. Accordingly, the connection portions 12 are disposed between the adjacent ring portions 11A, 11B in a comparatively compact state.

Note that in the stent 10, the cylindrical (tubular) main body portion 15 is formed from the ring portions 11 and the connection portions 12 described above.

As described above, in the stent 10, the main body portion 15 is provided with only two of the ring portions 11. Therefore, the stent 10 is a short stent, in which the length of the main body portion 15 in the axial direction is short. For that reason, even if the stent 10 is implanted in a body part that moves in a plurality of directions, such as a leg, the occurrence of damage in conjunction with the movement is inhibited. In the present embodiment, a length L in the axial direction of the main body portion 15 is set to 4.5 millimeters. Further, an outside diameter D of the main body portion 15 is set to 5 millimeters, so the ratio L/D of the axial direction length L and the outside diameter D is 0.9.

Note that the axial direction length L of the main body portion 15 does not necessarily have to be 4.5 millimeters, and the dimension ratio L/D does not necessarily have to be 0.9. However, from the standpoint of inhibiting damage to the stent 10, it is preferable for L to be from 3 to 40 millimeters, and it is preferable for L/D to be from 0.2 to 30.

As described previously, in a case where detachment occurs in a blood vessel wall inside the body (inside a tubular cavity), the stent 10 is what is used to support the detached portion. The stent 10 that is used for this sort of purpose does not need as great an expansive force as the general-purpose stent that is used for the purpose of a procedure to dilate a constricted location. Therefore, in the stent 10, the expansive force is set to 4 to 7 N/cm.

The marker attachment portion 16 is linked to each end of the main body portion 15 in the axial direction in order to attach a marker 19 (refer to FIG. 3) for imaging. The marker attachment portion 16 is formed from a linear element into a circular ring shape. The marker attachment portion 16 is linked to each one of the ring portions 11A, 11B through a leg portion 17 that is made from a short linear element. More specifically, the marker attachment portion 16 is linked through the leg portion 17 to each one of the apices 11b of the ring portions 11A, 11B.

The marker attachment portion 16 that is linked to the ring portion 11A is disposed such that it projects away from the ring portion 11A in the axial direction. The marker attachment portion 16 that is linked to the ring portion 11B is disposed such that it projects away from the ring portion 11B in the axial direction. Each one of the marker attachment portions 16 is disposed such that its central axis is turned toward the axis line (specifically, an extension of the axis line) of the main body portion 15. More specifically, each one of the marker attachment portions 16 is disposed such that an extension of its central axis intersects the axis line (specifically, the extension of the axis line) of the main body portion 15.

A plurality of the marker attachment portions 16 are disposed along the circumferential direction of the ring portions 11A, 11B. In the present embodiment, two of the marker attachment portions 16 are provided on each one of the ring portions 11A, 11B. The marker attachment portions 16 are disposed at specified intervals in the circumferential direction. In the present embodiment, the marker attachment portions 16 are disposed at equal intervals (180-degree intervals). The marker attachment portions 16 that are provided on the ring portion 11A are disposed in positions that are offset in the circumferential direction from the positions of the marker attachment portions 16 that are provided on the ring portion 11B. Specifically, the marker attachment portions 16 on the ring portion 11A are disposed such that, in the circumferential direction, they are positioned midway between the marker attachment portions 16 on the ring portion 11B. Therefore, when the marker attachment portions 16 on the ring portions 11A, 11B are viewed from the axial direction, the marker attachment portions 16 on the ring portion 11A and the marker attachment portions 16 on the ring portion 11B are disposed such that they are arrayed in alternation at equal intervals along the circumferential direction.

Note that the arrangement of the marker attachment portions 16 is not necessarily limited to the arrangement described above. For example, the marker attachment portions 16 on the ring portion 11A and the marker attachment portions 16 on the ring portion 11B may also be disposed in the same positions in the circumferential direction. It is also not absolutely necessary for two of the marker attachment portions 16 to be disposed on each one of the ring portions 11A, 11B. The number of the marker attachment portions 16 that are disposed on each one of the ring portions 11A, 11B may also be one, and it may also be equal to or more than three. Furthermore, different numbers of the marker attachment portions 16 may also be provided on the ring portions 11A, 11B.

Each one of the plurality of the marker attachment portions 16 is formed into a ring shape. The marker 19 is mounted in the opening on the inner side of each one of the marker attachment portions 16. The marker 19 is made from a metal material that is impermeable to X-rays and is formed into a disc shape. The marker 19 may be formed from platinum, for example. The outside diameter of the marker 19 is substantially the same as the inside diameter of the marker attachment portion 16. The marker 19 is mounted in a state in which it is fitted into the inner side of the marker attachment portion 16. Note that the marker 19 may also be formed from a metal material other than platinum, such as gold, a cobalt-chromium alloy, or the like.

In the present embodiment, the marker attachment portion 16 is provided with a position shift inhibition function that inhibits shifting of the position of the stent 10. Next, the position shift inhibition function will be explained.

The leg portion 17, which links the marker attachment portion 16 to the ring portion 11, includes a bent portion 21. Each one of the plurality of the leg portions 17 includes the bent portion 21. The bent portion 21 is a portion that is bent such that the marker attachment portion 16 is inclined toward the outer side of the main body portion 15 in the radial direction. Because the bent portion 21 is provided in the leg portion 17, the marker attachment portion 16 is in a state in which it is inclined in relation to the axial direction and tilts outward in the radial direction of the ring portion 11 (the main body portion 15). The tilting of the marker attachment portion 16 in this manner causes the entire marker attachment portion 16 to be positioned (extended) to the outside from the main body portion 15 in the radial direction. Note that in FIG. 3, the bent portion 21 is shown in an opened state.

The inclination angle γ of the marker attachment portion 16 in relation to the axial direction of the main body portion 15 is set to 15 degrees. The inclination angle γ does not necessarily have to be set to 15 degrees. It is preferable for the inclination angle γ to be set from 5 to 45 degrees, and even more preferable for it to be set from 10 to 30 degrees.

A plurality of projecting portions 23 are provided on the outer edges of each one of the plurality of the marker attachment portions 16. In the present embodiment, two of the projecting portions 23 are provided on each one of the marker attachment portions 16. The projecting portions 23 are provided on the opposite side of the marker attachment portion 16 from the main body portion 15 in the inclination direction in which the marker attachment portion 16 is tilted, and the projecting portions 23 project from the outer edge of the marker attachment portion 16 toward the opposite side from the main body portion 15. Hereinafter, the direction in which the marker attachment portion 16 tilts in relation to the axial direction of the main body portion 15 will be called the inclination direction X. The projecting portions 23 are disposed such that they are aligned in a circumferential direction of the marker attachment portion 16. More specifically, the projecting portions 23 are disposed such that, in a case where a virtual line is posited that extends in the inclination direction X through the center of the marker attachment portion 16, the projecting portions 23 are symmetrically disposed on opposite sides of the virtual line.

The projecting portion 23 is formed into a triangular shape. The projecting portion 23 has a shape that narrows toward an apex, which is where a projecting tip is located. A projection height H, which is the distance that the projecting portion 23 projects from the marker attachment portion 16, is substantially the same as a wire diameter of the marker attachment portion 16. However, the projection height H of the projecting portion 23 may also be greater than the wire diameter of the marker attachment portion 16, and it may also be less than the wire diameter.

Figure 4A:
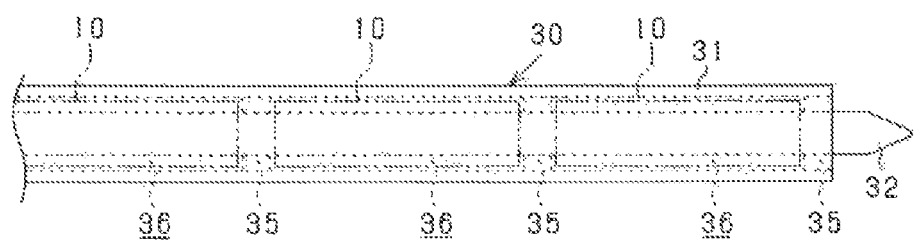
FIGS. 4A and 4B are side views that show the configuration of a catheter for transport, FIG. 4A showing a state in which the individual stents are housed inside the transport catheter in a contracted state, and FIG. 4B showing a state in which some of the stents have come out of the transport catheter and expanded.
Figure 4B:
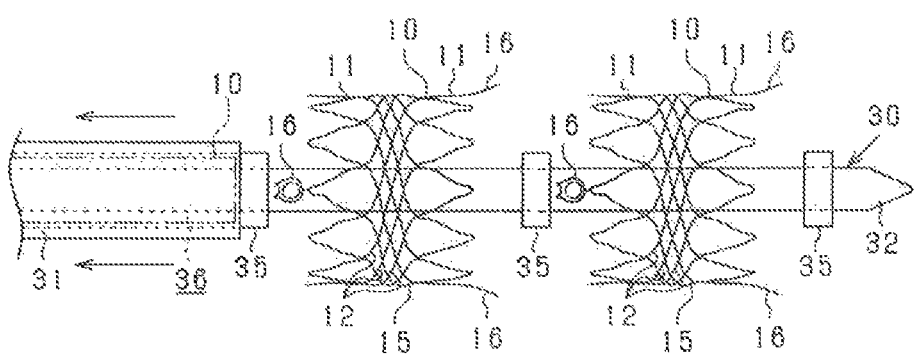

A stent transport catheter, which is used for introducing (transporting) the stent 10 described above into the body, will be explained. A plurality of the stents 10 can be loaded into the transport catheter. In the present embodiment, an example will be used in which a plurality of the stents 10 are transported into the body using the transport catheter. FIGS. 4A and 4B are side views that show the configuration of the transport catheter. FIG. 4A shows a state in which the individual stents 10 are housed inside the transport catheter in a contracted state. FIG. 4B shows a state in which some of the stents 10 have come out of the transport catheter and expanded. In FIGS. 4A and 4B, the left side and the right side are respectively the base end side and the leading end side of the transport catheter. As shown in FIGS. 4A and 4B, a transport catheter 30 is provided with a tubular outer shaft 31 and a tubular inner shaft 32. Both of the shafts 31, 32 are formed from a resin material. The inner shaft 32 is inserted into the interior of the outer shaft 31. The outer shaft 31 is configured to be displaced in the axial direction in relation to the inner shaft 32 in the inserted state.

A plurality of circular ring-shaped stoppers 35, which project from the outer circumferential face of the inner shaft 32, are provided on the leading end side of the inner shaft 32. The plurality of the stoppers 35 are disposed at specified intervals (specifically, at equal intervals) along the axial direction of the inner shaft 32. In this case, the intervals between the stoppers 35 are set to a dimension that is the same as or slightly greater than the axial direction length of the stent 10 in its contracted state.

In the interior of the outer shaft 31, the areas between the stoppers 35 serve as stent housing areas 36 for contracting the stents 10. One of the stent housing areas 36 is provided between every pair of the stoppers 35. Accordingly, a plurality (for example, four) of the stent housing areas 36 are provided along the axial direction in the interior of the outer shaft 31.

The stents 10 in the contracted state are housed in the stent housing areas 36 (refer to FIG. 4A). In the contracted state, the stents 10 are covered from the outer side by the outer shaft 31. The stents 10 are in a state in which their expansion to the outside in the radial direction is restricted by the outer shaft 31. The contracted state of the stents 10 is thus maintained. Note that in the state in which the stents 10 are housed in the corresponding stent housing areas 36 (in other words, the state that is shown in FIG. 4A), the position of the outer shaft 31 in relation to the inner shaft 32 is the initial position of the outer shaft 31. Furthermore, for the sake of convenience, in FIGS. 4A and 4B, the stents 10 that are housed in the contracted state in the stent housing areas 36 are indicated in simplified form by rectangles drawn with two-dot chain lines.

When the outer shaft 31 is displaced toward the base end side from the initial position in relation to the inner shaft 32, as shown in FIG. 4B, the stents 10 that are housed in the stent housing areas 36 emerge from the outer shaft 31 at the leading end side. The emerged stents 10 are thus decompressed (changed in shape) from the contracted state to the expanded state by their own elastic force (recovering elastic force).

Note that a stent delivery catheter is configured by the providing of the transport catheter 30 and the stents 10.

Next, an operation by which the stent 10 is implanted in the body will be explained with reference to FIGS. 5A to 5E. FIGS. 5A to 5E are explanatory figures for explaining the operation. In the present embodiment, an example will be used in which a balloon catheter has been used to perform a dilation procedure on a constricted location that has formed in a peripheral blood vessel in the leg, after which the stent 10 is implanted in the peripheral blood vessel so that a portion that has become detached during the dilation procedure will be supported by the stent 10. In FIGS. 5A to 5E, the left side and the right side are respectively the base end side and the leading end side of the transport catheter.

Figure 5A:
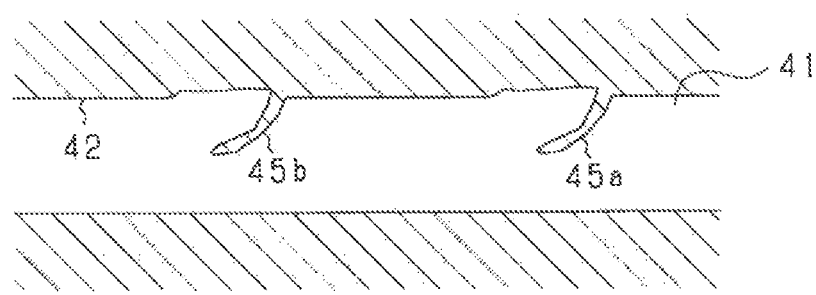
FIGS. 5A, 5B, 5C, 5D, and 5E are explanatory figures for explaining an operation by which the stent is implanted in a body.

FIG. 5A shows a blood vessel 41 (a peripheral blood vessel) in the leg after the dilation procedure has been performed using the balloon catheter. As shown in FIG. 5A, during the dilation procedure, detachment has occurred in a plurality of locations (specifically, two locations) in a blood vessel wall 42 of the blood vessel 41, and detached portions 45a, 45b are in a state of having peeled away from the blood vessel wall 42.

Figure 5B:
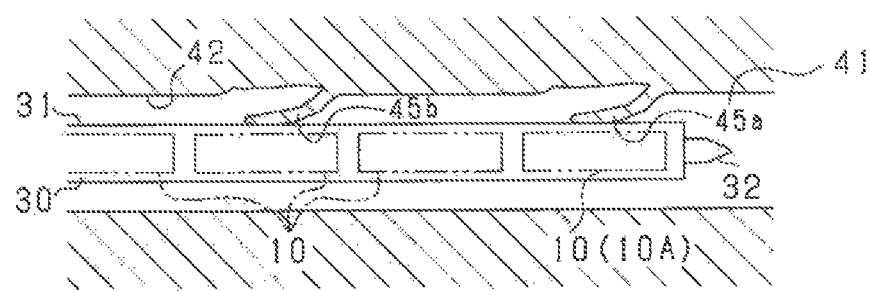

Under the circumstances in which this sort of detachment has occurred in the blood vessel wall 42, the transport catheter 30, in which the plurality of the stents 10 are housed, is introduced into the blood vessel 41 (refer to FIG. 5B). When the transport catheter 30 is introduced, the stent 10 (hereinafter called the stent 10A) that, among the plurality of the stents 10 that are housed in the transport catheter 30, is disposed the closest to the leading end side is disposed such that it is aligned with the detached portion 45a, which is the one of the detached portions 45a, 45b that is deeper inside the blood vessel 41. Note that when the transport catheter 30 is introduced, the position of the outer shaft 31 in relation to the inner shaft 32 is set to the initial position.

Figure 5C:
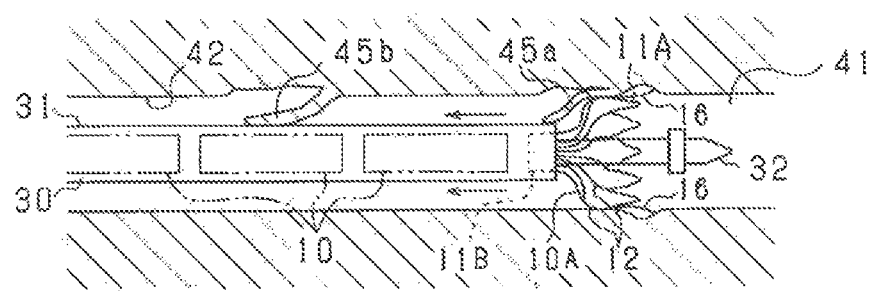

Next, as shown in FIG. 5C, the outer shaft 31 is displaced from the initial position toward the base end side in relation to the inner shaft 32, and a portion of the stent 10A emerges from the outer shaft 31 at the leading end side. Specifically, at this point, the ring portion 11 and the connection portions 12 on the leading end side of the stent 10A have emerged from the outer shaft 31, and the ring portion 11 on the base end side of the stent 10A remains housed inside the outer shaft 31. Thus, of the ring portions 11, only the ring portion 11 on the leading end side has expanded outward in the radial direction, such that the ring portion 11 is positioned inside the blood vessel 41 in the expanded state. Note that in the explanation that follows, the ring portion 11 on the leading end side will be called the ring portion 11A, and the ring portion 11 on the base end side will be called the ring portion 11B.

As the ring portion 11A expands, the connection portions 12 are put into a state in which they connect the ring portion 11A in the expanded state and the ring portion 11B, which is in the contracted state and housed inside the outer shaft 31. At this time, each one of the connection portions 12 is in an inclined state in relation to the axial direction, such that it expands outward in the radial direction from the base end side toward the leading end side.

Here, in the stent 10, as described previously, the length of each one of the connection portions 12 is sufficiently longer than the distance between the adjacent ring portions 11A, 11B. Specifically, each one of the connection portions 12 has a length that makes it able to connect the ring portion 11A in the expanded state to the ring portion 11B in the contracted state. Therefore, when the ring portion 11A (specifically, only the ring portion 11A) expands, a problem in which the expansion is restricted by the connection portions 12 is avoided. The result is that the ring portion 11A is positioned inside the blood vessel 41 in a sufficiently expanded state. The ring portion 11A is thus positioned inside the blood vessel 41 in a stable state.

Furthermore, in the state in which the ring portion 11A is disposed inside the blood vessel 41, the marker attachment portions 16 that are linked to the ring portion 11A enter a state in which they dig into the blood vessel wall 42. Therefore, in this respect as well, the ring portion 11A is positioned inside the blood vessel 41 in a stable state.

Figure 5D:
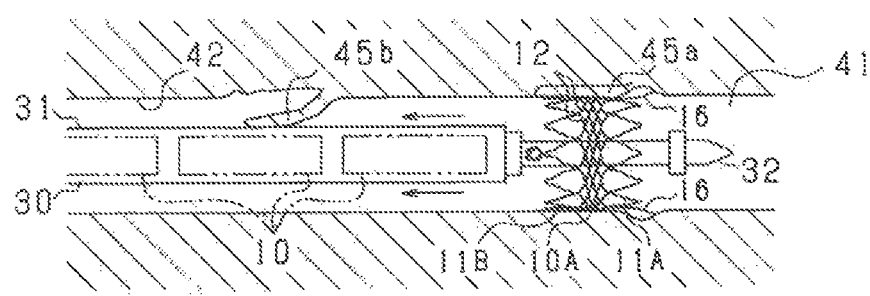

Next, as shown in FIG. 5D, the outer shaft 31 is displaced farther toward the base end side in relation to the inner shaft 32, and the ring portion 11B of the stent 10A emerges from the outer shaft 31. In other words, the entire stent 10A emerges from the outer shaft 31. The ring portion 11B thus expands outward in the radial direction, and the entire stent 10A enters the expanded state. The stent 10A is then implanted in the blood vessel 41 in the expanded state. At this time, the detached portion 45a is pressed against the blood vessel wall 42 by the main body portion 15 of the stent 10A. The detached portion 45a enters a state of being supported by the main body portion 15. Therefore, the occurrence of a problem in which the blood vessel 41 is obstructed by the detached portion 45a may be inhibited.

Furthermore, in the stent 10, as described previously, the inclination angle α of each one of the connection portions 12 is smaller than the inclination angle β (refer to FIG. 3). Therefore, the connection portions 12 are disposed compactly between the adjacent ring portions 11. This makes it possible for the detached portion 45a to be supported particularly well by each one of the connection portions 12.

Furthermore, with the stent 10A in the implanted state, the individual marker attachment portions 16 that are linked to the ring portions 11A, 11B are in a state of digging into the blood vessel wall 42 of the blood vessel 41. The stent 10A may thus be inhibited from shifting position inside the blood vessel 41. It is therefore possible to inhibit the occurrence of a problem such as the detached portion 45a ceasing to be supported due to a shift in the position of the stent 10A.

Furthermore, when the ring portion 11B expands, the ring portion 11A is already disposed inside the blood vessel 41 in a stable state, as stated previously, so it is possible to inhibit any shifting of the position of the ring portion 11A (as well as the entire stent 10A) inside the blood vessel 41 as the ring portion 11B expands, specifically shifting that is due to the force (the energizing force) of the ring portion 11B's expansion. It is therefore possible to implant the stent 10A in the desired position in a stable state.

Figure 5E:
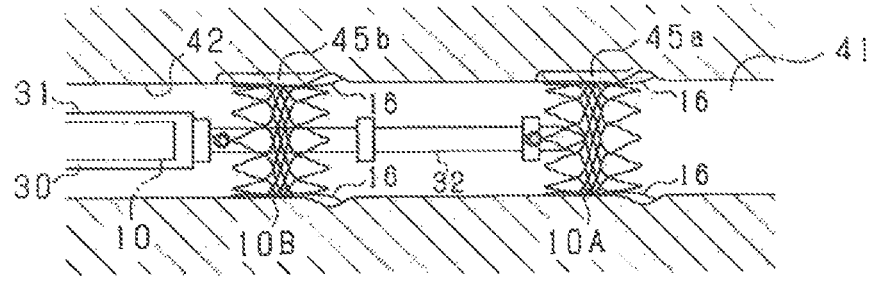

Next, as shown in FIG. 5E, the transport catheter 30 is moved toward the base end side, and the stent 10 (hereinafter called the stent 10B) that, among the plurality of the stents 10 that are housed in the transport catheter 30, is disposed the closest to the leading end side is disposed such that it is aligned with the detached portion 45b. Then the stent 10B is implanted inside the blood vessel 41 by the same procedure by which the stent 10A was implanted, as described above. The detached portion 45b is thus pressed against the blood vessel wall 42 by the stent 10B in the expanded state, such that the detached portion 45b enters a state of being supported by the stent 10B.

As described previously, after the stents 10A, 10B are implanted inside the blood vessel 41, the transport catheter 30 is withdrawn from inside the blood vessel 41. With that, the sequence of operations is finished.

As described above, the transport catheter 30 is provided with the outer shaft 31 and the inner shaft 32, and configured to be loaded with at least one of the stents 10. The stent 10 is configured such that, in the state in which the entire ring portion 11A has emerged from the outer shaft 31 and the entire ring portion 11B is covered by the outer shaft 31, the ring portion 11B does not move in the axial direction. That is, the stent 10 is configured such that the ring portion 11A does not shift position inside the blood vessel 41 under the force of the ring portion 11B's expansion. This makes it possible for a user such as a doctor or the like to place the stent 10 in the desired position in a stable state when using the transport catheter 30 to place the stent 10 inside the blood vessel 41.

The configuration of the present embodiment that is explained in detail above produces the superior results hereinafter described.

By including the bent portion 21 in the leg portion 17 that links the marker attachment portion 16 to the main body portion 15, the marker attachment portion 16 tilts outward in the radial direction of the main body portion 15. The marker attachment portion 16 may thus dig into the blood vessel wall 42 when the stent 10 is implanted in the blood vessel 41. This makes it possible to inhibit any shifting of the position of the stent 10.

Furthermore, with the configuration that thus inhibits shifting of the position of the stent 10 by tilting the marker attachment portion 16, there is no particular need to make any modifications to the shape or the like of the main body portion 15. Therefore, shifting of the position of the stent 10 may be inhibited without making the configuration of the stent 10 more complex.

The marker attachment portions 16, which are linked to both ends of the main body portion 15 in the axial direction, are tilted outward in the radial direction of the main body portion 15. It is therefore possible to cause the individual marker attachment portions 16 on both ends of the main body portion 15 to dig into the blood vessel wall 42 inside the blood vessel 41 when the stent 10 is implanted in the body. It is thus possible to inhibit shifting of the position of the stent 10 even more effectively.

Each one of the plurality of the marker attachment portions 16 that are disposed at specified intervals in the circumferential direction of the main body portion 15 is tilted outward in the radial direction of the main body portion 15. It is therefore possible to cause each one of the plurality of the marker attachment portions 16 to dig into the blood vessel wall 42 inside the blood vessel 41 when the stent 10 is implanted in the body. It is thus possible to inhibit shifting of the position of the stent 10 more effectively.

The projecting portions 23, which project toward the opposite side of the marker attachment portion 16 from the main body portion 15 in the inclination direction X in which the marker attachment portions 16 are tilted, are formed on the outer edges of the marker attachment portions 16. In this case, the projecting portions 23 may increase the degree to which the marker attachment portions 16 are anchored to the blood vessel wall 42 inside the blood vessel 41. The effect of inhibiting shifting of the position of the stent 10 is therefore enhanced.

In a case where the ring portions 11 all have the same configuration, the surface area where a stent that is provided with only two of the ring portions 11 (a short stent) is in contact with the blood vessel wall is less than the surface area where a stent that is provided with equal to or more than three of the ring portions 11 is in contact with the blood vessel wall. The smaller the surface area of contact with the blood vessel wall, the more readily the stent shifts position in the axial direction. In light of that point, in the embodiment that is described above, the short-sized stent 10 (the short stent) that is provided with only two of the ring portions 11 includes the function that uses the marker attachment portions 16 described above to inhibit any shifting of position. Therefore, even in the short-sized stent 10, shifting of the position of the stent 10 may be inhibited well.

Furthermore, with the stent 10, which is used to support the detached portions 45a, 45b that have formed in the blood vessel wall 42 of the blood vessel 41, not as great an expansion force is needed as is necessary for a stent that is used to expand a constricted portion. Therefore, the expansion force of this sort of the stent 10 is set to be comparatively small. Therefore, with the stent 10, shifting of position inside the blood vessel 41 is thought to occur more readily than with a stent that is used to expand a constricted portion. In light of this point, in the embodiment that is described above, the stent 10 is provided with the function that uses the marker attachment portions 16 described above to inhibit any shifting of position, so shifting of position may be inhibited well, even if the stent 10 has a small expansion force.

The present disclosure is not limited to the embodiment that is described above, and it may also be implemented as hereinafter described, for example.

(1) In the embodiment that is described above, the stent 10 is configured such that all of the plurality of the marker attachment portions 16 tilt outward in the radial direction. However, it is also acceptable for only a portion of the plurality of the marker attachment portions 16 to tilt outward in the radial direction. For example, of the plurality of the marker attachment portions 16 that are provided on the ring portion 11A, it is acceptable for only a portion (for example, one) of the marker attachment portions 16 to tilt outward in the radial direction, and of the plurality of the marker attachment portions 16 that are provided on the ring portion 11B, it is acceptable for only a portion (for example, one) of the marker attachment portions 16 to tilt outward in the radial direction.

Of a plurality of the ring portions 11A, 11B, it is acceptable for only the marker attachment portions 16 that are provided on the ring portion 11A (or the ring portion 11B) to tilt outward in the radial direction. Among a plurality of the marker attachment portions 16, it is also acceptable for only one of the marker attachment portions 16 to be provided such that it tilts outward in the radial direction. In other words, among the plurality of the marker attachment portions 16, it is acceptable for the bent portion 21 to be provided in the linkage portion between the main body portion 15 and only one of the marker attachment portions 16. Even in that case, shifting of the position of the stent 10 may be inhibited by the one marker attachment portion 16.

Figure 6A:
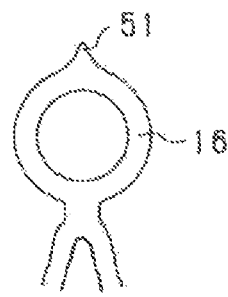
FIGS. 6A, 6B, and 6C are figures that show different forms of a projecting portion.
Figure 6B:
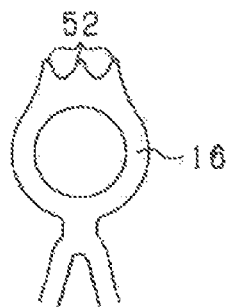

(2) In the embodiment that is described above, two of the projecting portions 23 are provided on each one of the marker attachment portions 16, but the number of the projecting portions 23 is not necessarily limited to two. For example, it is acceptable for only one projecting portion 51 to be provided on the marker attachment portion 16, as shown in FIG. 6A, and three projecting portions 52 may also be provided, as shown in FIG. 6B.

Furthermore, in the embodiment that is described above, the projecting portions 23 are provided on each one of the marker attachment portions 16, but it is acceptable for the projecting portions 23 to be provided on only a portion of the marker attachment portions 16. It is also acceptable for the projecting portions 23 to be provided on none of the marker attachment portions 16. Even in that case, shifting of the position of the stent 10 may be inhibited by causing the marker attachment portions 16 to dig into the blood vessel wall 42.

Figure 6C:
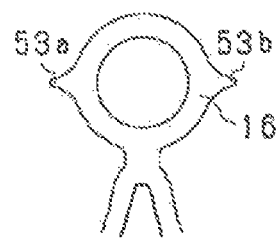

(3) In the embodiment that is described above, the projecting portions 23 are provided on the marker attachment portion 16 such that they project from the outer edge of the marker attachment portion 16 in the inclination direction X toward the opposite side from the main body portion 15, but the projecting portions may also be provided such that they project in a different direction. For example, as shown in FIG. 6C, projecting portions 53 may be provided on the marker attachment portion 16 that project from the outer edge in the circumferential direction of the main body portion 15. In the example in FIG. 6C, a projecting portion 53a that projects toward one side in the circumferential direction and a projecting portion 53b that projects toward the other side in the circumferential direction are provided as the projecting portions 53.

According to this configuration, in a case where the stent 10 tends to rotate around its axis line inside the blood vessel 41, the rotation of the stent 10 may be inhibited by the catching of the projecting portions 53a, 53b on the blood vessel wall 42. In a case where the connection portions 12 of the stent 10 extend in the direction in which they are inclined in relation to the axial direction and the circumferential direction, there is a possibility that the connection portions 12 acts as screw threads if the stent 10 rotates. When the connection portions 12 act as screw threads, there is a possibility that the stent 10 moves in the axial direction as it rotates. Therefore, inhibiting the rotation of the stent 10 in this manner makes it possible to inhibit the shifting of the position of the stent 10 that accompanies the rotation.

Note that the projecting portions 53 may also be provided on the marker attachment portion 16 instead of the projecting portions 23 in the embodiment that is described above, and the projecting portions 53 may also be provided in addition to the projecting portions 23. Furthermore, in the same manner as the projecting portions 23, the projecting portions 53 may be provided on each one of the plurality of the marker attachment portions 16, and they may also be provided on only a portion of the plurality of the marker attachment portions 16.

(4) In the embodiment that is described above, the marker 19 is mounted in each one of the plurality of the marker attachment portions 16. However, it is also acceptable for the markers 19 to be mounted in only a portion of the plurality of the marker attachment portions 16. In that case, the marker attachment portions 16 in which the markers 19 are not mounted function only to inhibit shifting of the positions of the stents 10.

(5) In the embodiment that is described above, the marker attachment portion 16 has a circular ring shape, but the marker attachment portion may also have a different ring shape, such as an elliptical ring, a rectangular ring, a triangular ring, or the like. Further, the marker attachment portion does not necessarily have to have a ring shape, and it may also be formed into an open shape such as a U shape, a C shape, or the like. In that case, the marker may be mounted by being fitted into a slot in the marker attachment portion.

(6) In the embodiment that is described above, the stents 10A, 10B are introduced into the blood vessel 41 using a single insertion of the transport catheter 30, into which a plurality of the stents 10 can be loaded. However, the stents 10A, 10B may also be introduced using separate insertions of a transport catheter into which only one of the stents 10 can be loaded.

(7) The embodiment that is described above was explained using the short-sized stent 10 (the short stent) that is provided with two of the ring portions 11. However, the present disclosure may also be applied to a stent that is provided with equal to or more than three of the ring portions 11. Furthermore, the stents to which the present disclosure can be applied are not limited to a stent with configuration that is provided with ring portions and connection portions, and the present disclosure can also be applied to a stent with other configuration.

In the embodiment that is described above, the present disclosure is applied to the stent 10, which is used for the purpose of supporting the detached portions 45a, 45b that form in the blood vessel wall 42. However, the present disclosure may also be applied to a stent that is used for another purpose, such as dilating a constricted portion that has formed inside the body, for example. Furthermore, the application of the present disclosure is not limited to a self-expanding type of stent, and the present disclosure may also be applied to a balloon-expanded type of stent.

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. A stent comprising:
   a cylindrical main body portion extending in an axial direction;
   a plurality of linkage portions including a first linkage portion and a second linkage portion, the first linkage portion extending from an end of the main body portion in the axial direction, the second linkage portion extending from the other end of the main body portion in the axial direction; and
   a plurality of marker attachment portions configured such that a marker for imaging is fitted into an inner side of each one of the plurality of the marker attachment portions, the plurality of the marker attachment portions including a first marker attachment portion and a second marker attachment portion, the first marker attachment portion being linked to the main body portion only through the first linkage portion, the second marker attachment portion being linked to the main body portion only through the second linkage portion, wherein the first linkage portion includes a first bent portion tilting the first marker attachment portion outward in a radial direction of the main body portion, and the second linkage portion includes a second bent portion tilting the second marker attachment portion outward in the radial direction of the main body portion, and wherein the main body portion includes:
 a plurality of ring portions arrayed in the axial direction and forming rings centered on an axis line of the main body portion, and
 a plurality of connection portions disposed at specified intervals in a circumferential direction of the main body portion, the plurality of connection portions connecting the plurality of the ring portions, each one of the plurality of connection portions connecting two of the plurality of ring portions adjacent to one another in the axial direction, wherein the plurality of the connection portions extends in a specified direction, the specified direction including a component of the axial direction and a component of the circumferential direction, and wherein the specified direction is a direction whose inclination in relation to the circumferential direction is less than its inclination in relation to the axial direction.

2. The stent according to claim 1, further comprising:
a plurality of the first marker attachment portions disposed at specified intervals in the circumferential direction of the main body portion;
a plurality of the second marker attachment portions disposed at specified intervals in the circumferential direction of the main body portion;
a plurality of the first linkage portions respectively linked to the plurality of the first marker attachment portions; and
a plurality of the second linkage portions respectively linked to the plurality of the second marker attachment portions,
wherein each one of the plurality of the first linkage portions includes the first bent portion, and each one of the plurality of the second linkage portions includes the second bent portion.

3. The stent according to claim 2, wherein
a first projecting portion is provided on each one of the plurality of the first marker attachment portions, the first projecting portion projecting toward an opposite side of each one of the plurality of the first marker attachment portions from the main body portion side in a first inclination direction, the first inclination direction being a direction in which each one of the plurality of the first marker attachment portions is tilted in relation to the axial direction.

4. The stent according to claim 3, wherein
a second projecting portion is provided on each one of the plurality of the second marker attachment portions, the second projecting portion projecting toward an opposite side of each one of the plurality of the second marker attachment portions from the main body portion side in a second inclination direction, the second inclination direction being a direction in which each one of the plurality of the second marker attachment portions is tilted in relation to the axial direction.

5. The stent according to claim 4, wherein
each one of the plurality of the second marker attachment portions is a circular ring shape having a hole into which the marker for imaging is fitted, and
each one of the second projecting portions projects from an outer peripheral surface of each one of the plurality of the second marker attachment portions.

6. The stent according to claim 5, wherein
each one of the second projecting portions is a triangular shape that narrows toward an apex that is where a projecting tip is located.

7. The stent according to claim 3, wherein
each one of the plurality of the first marker attachment portions is a circular ring shape having a hole into which the marker for imaging is fitted, and
each one of the first projecting portions projects from an outer peripheral surface of each one of the plurality of the first marker attachment portions.

8. The stent according to claim 7, wherein
each one of the first projecting portions is a triangular shape that narrows toward an apex that is where a projecting tip is located.

9. The stent according to claim 2, wherein
a first projecting portion is provided on each one of the plurality of the first marker attachment portions, the first projecting portion projecting in the circumferential direction of the main body portion.

10. The stent according to claim 9, wherein
a second projecting portion is provided on each one of the plurality of the second marker attachment portions, the second projecting portion projecting in the circumferential direction of the main body portion.

11. The stent according to claim 10, wherein
each one of the plurality of the second marker attachment portions is a circular ring shape having a hole into which the marker for imaging is fitted, and
each one of the second projecting portions projects from an outer peripheral surface of each one of the plurality of the second marker attachment portions.

12. The stent according to claim 11, wherein
each one of the second projecting portions is a triangular shape that narrows toward an apex that is where a projecting tip is located.

13. The stent according to claim 9, wherein
each one of the plurality of the first marker attachment portions is a circular ring shape having a hole into which the marker for imaging is fitted, and
each one of the first projecting portions projects from an outer peripheral surface of each one of the plurality of the first marker attachment portions.

14. The stent according to claim 13, wherein
each one of the first projecting portions is a triangular shape that narrows toward an apex that is where a projecting tip is located.

\* \* \* \* \*